(12) United States Patent
Sappok et al.

(10) Patent No.: US 10,260,400 B2
(45) Date of Patent: Apr. 16, 2019

(54) RADIO FREQUENCY SYSTEM AND METHOD FOR MONITORING ENGINE-OUT EXHAUST CONSTITUENTS

(71) Applicant: CTS Corporation, Lisle, IL (US)

(72) Inventors: Alexander G. Sappok, Cambridge, MA (US); Paul A. Ragaller, Dorchester, MA (US); Leslie Bromberg, Sharon, MA (US); Andrew D. Herman, Granger, IN (US)

(73) Assignee: CTS Corporation, Lisle, IL (US)

( * ) Notice: Subject to any disclaimer, the term of this patent is extended or adjusted under 35 U.S.C. 154(b) by 0 days.

(21) Appl. No.: 15/481,670

(22) Filed: Apr. 7, 2017

(65) Prior Publication Data

US 2017/0211453 A1   Jul. 27, 2017

Related U.S. Application Data

(63) Continuation-in-part of application No. 14/733,525, filed on Jun. 8, 2015, and a continuation-in-part of application No. 14/733,486, filed on Jun. 8, 2015.
(Continued)

(51) Int. Cl.
*H04B 1/18* (2006.01)
*F01N 11/00* (2006.01)
(Continued)

(52) U.S. Cl.
CPC .......... *F01N 11/00* (2013.01); *B01D 53/9422* (2013.01); *B01D 53/9495* (2013.01);
(Continued)

(58) Field of Classification Search
CPC ...... F02C 6/04; F02C 9/00; F02C 3/14; F02C 3/22; F02C 3/24; F02C 9/266
(Continued)

(56) References Cited

U.S. PATENT DOCUMENTS

| 4,024,452 A | 5/1977 | Seidel |
| 4,042,879 A | 8/1977 | Ho et al. |

(Continued)

FOREIGN PATENT DOCUMENTS

| CN | 1032238 A | 4/1989 |
| CN | 101078692 A | 11/2007 |

(Continued)

OTHER PUBLICATIONS

Rights et al: "Title Preparation and characterisation of ceria particles," 2013; Retrieved from the Internet: URL:htts:// :: bra.ucc.ie/ bitstream/handle/10468/1141 /MorrisVNA_ PhD2013 .pdf.

*Primary Examiner* — Tu X Nguyen
(74) *Attorney, Agent, or Firm* — Daniel Deneufbourg

(57) ABSTRACT

A radio frequency system and method for monitoring an engine-out exhaust emission constituent. The system comprises a housing containing the emission constituent, one or more radio frequency sensors extending into the housing and transmitting and receiving radio frequency signals, and a control unit for controlling the radio frequency signals and monitoring changes in the emission constituent based on changes in one or more parameters of the radio frequency signals. In one embodiment, the control unit measures a rate of change in one or more of the parameters of the radio frequency signals for monitoring a rate of change of the emission constituent including for example the emission rate, accumulation rate, and/or depletion rate of the emission constituent.

9 Claims, 6 Drawing Sheets

Related U.S. Application Data

(60) Provisional application No. 62/320,707, filed on Apr. 11, 2016.

(51) Int. Cl.

| | | |
|---|---|---|
| *H04B 17/18* | (2015.01) | |
| *H04B 17/309* | (2015.01) | |
| *B01D 53/94* | (2006.01) | |
| *F01N 3/20* | (2006.01) | |
| *G01N 22/04* | (2006.01) | |
| *H04W 24/08* | (2009.01) | |
| *F01N 3/021* | (2006.01) | |
| *G01N 15/00* | (2006.01) | |

(52) U.S. Cl.
CPC ............ *F01N 3/021* (2013.01); *F01N 3/208* (2013.01); *F01N 3/2066* (2013.01); *G01N 15/00* (2013.01); *G01N 22/04* (2013.01); *H04B 17/18* (2015.01); *H04B 17/309* (2015.01); *H04W 24/08* (2013.01); *B01D 2255/911* (2013.01); *F01N 2560/00* (2013.01); *F01N 2560/12* (2013.01); *F01N 2560/14* (2013.01); *F01N 2610/148* (2013.01)

(58) Field of Classification Search
USPC ......... 455/345, 193.2; 96/18, 109, 160, 161, 96/164
See application file for complete search history.

(56) References Cited

U.S. PATENT DOCUMENTS

| | | | |
|---|---|---|---|
| 4,477,771 A | 10/1984 | Nagy et al. | |
| 4,689,553 A | 8/1987 | Haddox | |
| 5,074,112 A | 12/1991 | Walton | |
| 5,103,181 A | 4/1992 | Gaisford et al. | |
| 5,142,595 A | 8/1992 | Chester | |
| 5,157,340 A | 10/1992 | Walton et al. | |
| 5,369,369 A | 11/1994 | Cutmore | |
| 5,423,180 A | 6/1995 | Nobue et al. | |
| 5,447,635 A | 9/1995 | Viscardi et al. | |
| 5,497,099 A | 3/1996 | Walton | |
| 5,500,599 A | 3/1996 | Stange | |
| 5,557,933 A | 9/1996 | Numata et al. | |
| 6,131,386 A | 10/2000 | Trumble | |
| 6,147,503 A | 11/2000 | Nelson et al. | |
| 6,507,308 B1 | 1/2003 | Ono et al. | |
| 6,630,833 B2 | 10/2003 | Scott | |
| 6,819,849 B1 | 11/2004 | Tangonan et al. | |
| 6,854,261 B2 | 2/2005 | Williamson et al. | |
| 7,157,919 B1 | 1/2007 | Walton | |
| 7,357,822 B2 | 4/2008 | Hamahata et al. | |
| 7,679,374 B2 | 3/2010 | Bromberg et al. | |
| 8,384,396 B2 | 2/2013 | Bromberg et al. | |
| 8,384,397 B2 | 2/2013 | Bromberg et al. | |
| 8,889,221 B2 | 11/2014 | Sappok | |
| 9,144,831 B2 | 9/2015 | Sappok et al. | |
| 9,399,185 B2 | 7/2016 | Bromberg et al. | |
| 9,400,297 B2 | 7/2016 | Bromberg et al. | |
| 2001/0003898 A1 | 6/2001 | Miller et al. | |
| 2001/0007571 A1 | 7/2001 | Murphy et al. | |
| 2002/0005725 A1 | 1/2002 | Scott | |
| 2004/0200198 A1 | 10/2004 | Inoue et al. | |
| 2005/0011278 A1 | 1/2005 | Brown et al. | |
| 2005/0213548 A1 | 9/2005 | Benson et al. | |
| 2005/0241295 A1 | 11/2005 | Breuer et al. | |
| 2006/0027511 A1 | 2/2006 | Brown et al. | |
| 2006/0070373 A1 | 4/2006 | Huang et al. | |
| 2006/0101793 A1 | 5/2006 | Gregoire et al. | |
| 2006/0138082 A1 | 6/2006 | Strang | |
| 2006/0229466 A1 | 10/2006 | Arhancet et al. | |
| 2007/0000218 A1 | 1/2007 | Wirth et al. | |
| 2007/0022746 A1 | 2/2007 | Decou et al. | |
| 2007/0024289 A1 | 2/2007 | Knitt et al. | |
| 2007/0056274 A1 | 3/2007 | Wills | |
| 2007/0068157 A1 | 3/2007 | Kurtz | |
| 2007/0072567 A1 | 5/2007 | Nagai et al. | |
| 2007/0101705 A1 | 5/2007 | Knitt | |
| 2007/0125075 A1 | 6/2007 | Zanini-Fisher et al. | |
| 2007/0125349 A1 | 6/2007 | Zanini-Fisher et al. | |
| 2007/0130923 A1 | 6/2007 | Dye et al. | |
| 2007/0169469 A1 | 7/2007 | Knitt | |
| 2007/0209333 A1 | 9/2007 | Kondou | |
| 2007/0214862 A1 | 9/2007 | Kubinski et al. | |
| 2008/0018442 A1 | 1/2008 | Knitt | |
| 2008/0059093 A1 | 3/2008 | Bromberg et al. | |
| 2008/0066621 A1 | 3/2008 | Naito et al. | |
| 2008/0092499 A1 | 4/2008 | Otsuka et al. | |
| 2008/0110143 A1 | 5/2008 | Chen et al. | |
| 2008/0264036 A1 | 10/2008 | Bellovary | |
| 2009/0038294 A1 | 2/2009 | Anderson et al. | |
| 2009/0295509 A1 | 12/2009 | Master et al. | |
| 2010/0101409 A1* | 4/2010 | Bromberg ............... F01N 3/025 95/8 |
| 2010/0102828 A1 | 4/2010 | Bromberg et al. | |
| 2012/0138093 A1 | 6/2012 | Sappok et al. | |
| 2013/0125745 A1 | 5/2013 | Bromberg et al. | |
| 2013/0127478 A1 | 5/2013 | Bromberg et al. | |
| 2013/0298530 A1 | 11/2013 | Carlill et al. | |
| 2014/0116028 A1 | 5/2014 | Sappok et al. | |
| 2015/0123688 A1 | 5/2015 | Sappok et al. | |
| 2015/0132187 A1 | 5/2015 | Takaoka et al. | |
| 2015/0355110 A1 | 12/2015 | Sappok et al. | |
| 2015/0358091 A1 | 12/2015 | Sappok et al. | |
| 2016/0109425 A1 | 4/2016 | Sappok et al. | |
| 2017/0182447 A1 | 6/2017 | Sappok et al. | |

FOREIGN PATENT DOCUMENTS

| | | |
|---|---|---|
| DE | 3317215 A1 | 11/1983 |
| DE | 102004016725 A1 | 2/2006 |
| EP | 0097416 A1 | 1/1984 |
| EP | 0356040 A2 | 2/1990 |
| JP | 4-505665 A | 10/1992 |
| WO | 92/02807 A1 | 2/1992 |
| WO | 93/05388 A1 | 3/1993 |
| WO | 00/50743 A1 | 8/2000 |
| WO | 2004/074670 A2 | 9/2004 |
| WO | 2005/060653 A2 | 7/2005 |
| WO | 2005/093233 A1 | 10/2005 |
| WO | 2006/002037 A2 | 1/2006 |
| WO | 2007/130896 A2 | 11/2007 |
| WO | 2009031600 A2 | 3/2009 |
| WO | 2010/074812 A1 | 7/2010 |
| WO | 2011/156477 A2 | 12/2011 |
| WO | 2014064406 A1 | 5/2014 |
| WO | 2015/188188 A1 | 12/2015 |
| WO | 2015/188189 A1 | 12/2015 |
| WO | 2017/165220 A1 | 9/2017 |

* cited by examiner

RADIO FREQUENCY SYSTEM AND
METHOD FOR MONITORING ENGINE-OUT
EXHAUST CONSTITUENTS

CROSS-REFERENCE TO RELATED APPLICATIONS

This patent application claims priority and benefit of the filing date of and is a continuation-in-part of U.S. patent application Ser. No. 14/733,525 filed on Jun. 8, 2015 and U.S. patent application Ser. No. 14/733,486 filed on Jun. 8, 2015, the disclosure and contents of which are expressly incorporated herein in their entireties by reference.

This patent application also claims priority and benefit of the filing date of U.S. Provisional Patent Application Ser. No. 62/320,707 filed on Apr. 11, 2016, the disclosure and contents of which is expressly incorporated herein in its entirety by reference.

GOVERNMENT SPONSORSHIP

This invention was made with government support under Award No. IIP 1330313 awarded by the National Science Foundation. The government has certain rights in the invention.

FIELD OF THE INVENTION

This invention relates to a radio frequency system and method for monitoring engine exhaust emissions constituents in an internal combustion engine or other process that generates emissions constituents such, as for example, particulate matter, gases or liquid constituents.

BACKGROUND OF THE INVENTION

Various means and methods are used today for monitoring emissions constituents in the exhaust of an internal combustion engine such as, for example, gasoline, diesel, natural gas, or other types of internal combustion engines, that utilize various emissions after-treatment devices such as an exhaust particulate filter, for example diesel particulate filters (DPF) and gasoline particulate filters (GPF), to reduce particulate matter emissions or various catalysts, traps, and scrubbers to reduce gaseous emissions, such as selective catalytic reduction systems (SCR), NOX traps, hydrocarbon traps, ammonia slip catalysts, oxidation catalysts, three-way catalysts, and the like.

Indirect methods (utilizing predictive models or so-called virtual sensors) have been employed to indirectly estimate engine emissions. These indirect methods have suffered from a number of shortcomings including for example the fact that these models are typically developed and calibrated given a specific set of boundary conditions or system inputs including, but not limited to, engine characteristics and operating parameters, fuel and lubricant type, aging factors, safety margins, and the like that require tuning to a specific set of input conditions which may not be universally applicable to all engines or systems and thus require some customization for each end-use application.

Virtual sensors that rely on these known set of operating conditions to accurately estimate engine emissions such as, for example, the composition, amount, rate, or concentration of the emissions in the exhaust have not by definition functioned appropriately over conditions or abnormal operation outside the capabilities of the predictive models.

Also, changes that occur to the engine as the engine ages and components wear or break down, or changes that occur to the catalysts as the catalysts age or become poisoned, cannot be dynamically captured utilizing predictive models. Generally, safety factors or deterioration factors are used to compensate for these changes resulting in a trade-off in overall performance that is generally too conservative when the engine is new in order to satisfy the system useful life requirements. The predictive model approach also suffers from the lack of any feedback mechanism to directly determine whether the system performance has degraded beyond the assumed safety margins. Moreover, the development, calibration, and tuning of the predictive models for a specific engine and application is time consuming and costly.

In the case of particulate filters, pressure or differential pressure sensors have also been used but they suffer from a lack of resolution and response. In particular, exhaust back-pressure or measurements of the particulate filter differential pressure are impacted by a wide range of noise factors including exhaust flow rate, temperature, particulate matter distribution, filter characteristics (hysteresis effects), and the like. Pressure measurements also do not provide a direct measure of particulate matter in the exhaust and lack the resolution to detect particulate matter build-up on the filter necessary to estimate engine-out PM emissions rates. Furthermore, pressure measurements are not reliable overall operating conditions, such as low flow (idle), with the engine off, during regeneration, or over transient events for example. This approach, therefore, does not provide a continuous measurement.

The use of pressure sensors also typically requires significant averaging or filtering to reduce the noise effects on the measurements. This signal averaging or filtering significantly increases the sensor's response time, making it unsuitable for any type of meaningful feedback control applications.

Soot sensors have also been used to measure the concentration of soot particles in the exhaust. Soot sensors however have a low measurement range thus resulting in a sensor that is quickly overwhelmed by the high levels of engine-out soot emissions. Also, soot sensors are designed to measure very low concentrations of soot in the exhaust gas stream (after the particulate filter) and are not suitable for measuring high levels of engine-out particulate matter emissions. Further, soot sensors only monitor a portion of the exhaust gas flow, and therefore do not provide a direct measurement of the total soot levels in the exhaust gas, but only the levels in the exhaust gas in close proximity to the sensor (or flowing through the sensor housing). Soot sensor accuracy is also affected by exhaust flow velocity, location of the sensing element in the exhaust pipe (as it only samples a small volume of the flow), temperature, particle morphology and composition, and accumulation of deposits (ash, catalyst/washcoat particles) as the sensor ages.

Accumulation type soot sensors have also been used. These sensors however do not provide a continuous monitor but rather cycle from a measuring state to a regeneration state. The regeneration state generally requires additional energy input to burn off any accumulated soot on the sensing element. The sensors also require condensate protection, which does not allow them to operate during certain conditions, such as cold start for example when they may be needed most. Accumulation type soot sensors further do not directly monitor the soot particle number or mass in the exhaust stream, but rather the time for a certain amount of material to accumulate on the sensing element, thereby providing only an indirect indication of soot levels in the exhaust. Soot sensors also suffer from poor durability, the accumulation of contaminants (such as ash), as well as thermal shock (water in the exhaust or condensation), which limits the sensor life and accuracy over its useful life. Due to the intermittent nature of the sensor operation which includes regeneration event followed by time period required for sufficient accumulation to generate a measurable response, these sensors also do not provide a continuous measurement.

A number of different types of gas sensors are also used, such as for example, NOx sensors, oxygen sensors, ammonia sensors, and other related sensors, which also suffer from many of the deficiencies described above. Many of these sensors use electrochemical cells to conduct the measurements. These types of sensing elements are fragile and may suffer from a number of failure modes in the field. In particular, it is well known that many gas sensors suffer from cross-sensitivities to other exhaust gas constituents, errors due to variations in the local gas velocity or flow rate near the sensing element, and temperature-related effects, among others. These sensors also sample only a portion of the exhaust flow and not the flow in its entirety. These sensors may also become poisoned due to contaminants in fuels, lubricants, or the environment. In another example, the sensor may become damaged when used in certain conditions. Many of these sensors also require significant energy input, such as from heaters, to enable their operation, and may not function over all operating conditions, such as changes in the air-fuel ratio in one example, or cold start conditions in another.

The present invention provides a direct, accurate, and fast response measurement of engine exhaust constituent levels using radio frequency measurements based on the interactions of the exhaust constituents with the emissions aftertreatment system, and directly addresses the deficiencies noted above.

The present invention further provides for a much simpler and more robust interface to the exhaust system, using only an antenna to transmit or receive the radio frequency signal to remotely probe or monitor the aftertreatment system (filter or catalyst) which itself serves as the sensor.

SUMMARY OF THE INVENTION

The present invention is directed to a radio frequency system for monitoring an engine-out exhaust emission constituent comprising a housing containing the emission constituent, one or more radio frequency sensors extending into the housing and transmitting and receiving radio frequency signals, and a control unit for controlling the radio frequency signals and monitoring changes in the emission constituent based on changes in one or more parameters of the radio frequency signals.

In one embodiment, the radio frequency signals span a radio frequency signal range and the control unit measures a change in one or more of the parameters of the radio frequency signals in predefined regions of the radio frequency signal range.

In one embodiment, the control unit measures changes in one or more of the parameters of the radio frequency signals in one or more predefined radio frequency signal ranges corresponding to one or more predefined spatial regions in the housing.

In one embodiment, the control unit measures changes in the magnitude or amplitude of the radio frequency signal and/or shifts in the phase of the radio frequency signal.

In one embodiment, one or more emission constituents are monitored by measuring changes in the magnitude and/or phase of the radio frequency signal in one or more predefined radio frequency signal ranges.

In one embodiment, the control unit measures a rate of change in one or more of the parameters of the radio frequency signals for monitoring a rate of change of the emission constituent.

In one embodiment, the power transmitted to the one or more radio frequency sensors is varied to improve the radio frequency signals.

In one embodiment, the control unit monitors the emission rate, accumulation rate, and/or depletion rate of the emission constituent.

The present invention is also directed to a method for monitoring an emission constituent in a radio frequency system including a housing containing the emission constituent, one or more radio frequency sensors extending into the housing and transmitting and receiving radio frequency signals; and a control unit, the method comprising the step of controlling the radio frequency signals and monitoring changes in the emission constituent based on changes in one or more parameters of the radio frequency signals.

In one embodiment, the radio frequency signals span a radio frequency signal range and further comprising the step of measuring a change in one or more of the parameters of the radio frequency signals in predefined regions of the radio frequency signal range.

In one embodiment, the step of measuring changes in one or more of the parameters of the radio frequency signals in one or more predefined radio frequency signal ranges corresponding to one or more predefined spatial regions in the housing.

In one embodiment, the predefined spatial regions correspond to predefined spatial regions sensitive to the parameter of the radio frequency signal being measured.

In one embodiment, the predefined spatial regions correspond to predefined spatial regions exhibiting a favorable behavior for the parameter of the radio frequency signal being measured.

In one embodiment, the step of sampling one or more of the parameters of the radio frequency signals in one or more predefined narrow radio frequency signal ranges to decrease the measurement response time.

In one embodiment, the one or more predefined narrow radio frequency signal ranges correspond to one or more predefined resonant modes of the radio frequency signal.

In one embodiment, the step of measuring changes in the magnitude or amplitude of the radio frequency signal and/or shifts in the phase of the radio frequency signal.

In one embodiment, one or more emission constituents are monitored by measuring changes in the magnitude and/or phase of the radio frequency signal in one or more predefined radio frequency signal ranges In one embodiment, the method further comprises the step of measuring a rate of change in one or more of the parameters of the radio frequency signals for monitoring a rate of change of the emission constituent.

In one embodiment, the method further comprises the step of comparing the rate of change of the emission constituent with expected values of the rate of change of the emission constituent.

In one embodiment, the method further comprises the step of monitoring the emission rate, accumulation rate, and/or depletion rate of the emission constituent.

Other advantages and features of the present invention will be more readily apparent from the following detailed description of the preferred embodiments of the invention, the accompanying drawings, and the appended claims.

BRIEF DESCRIPTION OF THE DRAWINGS

These and other features of the invention can best be understood by the description of the accompanying FIGS. as follows.

DETAILED DESCRIPTION OF THE EMBODIMENT

The invention relates to a radio frequency based system and method for monitoring engine-out exhaust emissions constituents as well as providing feedback control capabilities based on the monitored emissions.

For the purposes of this disclosure, the term emissions constituent refers to any solid, liquid, or gas phase emissions, whether resulting directly from the upstream process (such as combustion) as in the case of particulate matter constituents, or emission constituents introduced into the exhaust system through the use of additives or dosing, such as hydrocarbon or urea dosing in one example.

The terms particulate matter (PM) and soot are used interchangeably, and refer to particulate matter emission constituents which may contain carbon, hydrocarbons, sulfates, ash, or other materials. However, the invention is broadly applicable to monitoring the rates of emissions constituents in general, in which case particulate matter may be more broadly defined to include all types of solid or liquid particles or aerosols, and emissions constituents further includes any other type of gas or liquid phase emissions.

In a particular embodiment, a particulate filter such as a gasoline particulate filter (GPF) or diesel particulate filter (DPF) may be installed on a diesel or gasoline engine for any number of on- or off-road applications.

In another embodiment, a catalyst, such as a three-way catalyst (TWC), oxidation catalyst, selective catalytic reduction system (SCR), NOx trap or LNT, ammonia slip catalyst, hydrocarbon trap, or any other similar catalyst may be installed. The applications may include passenger cars, trucks, buses, construction equipment, agricultural equipment, power generators, ships, locomotives, and the like. In another example, the filter may be any type of suitable filter or catalyst installed on any suitable application.

Figure 1:
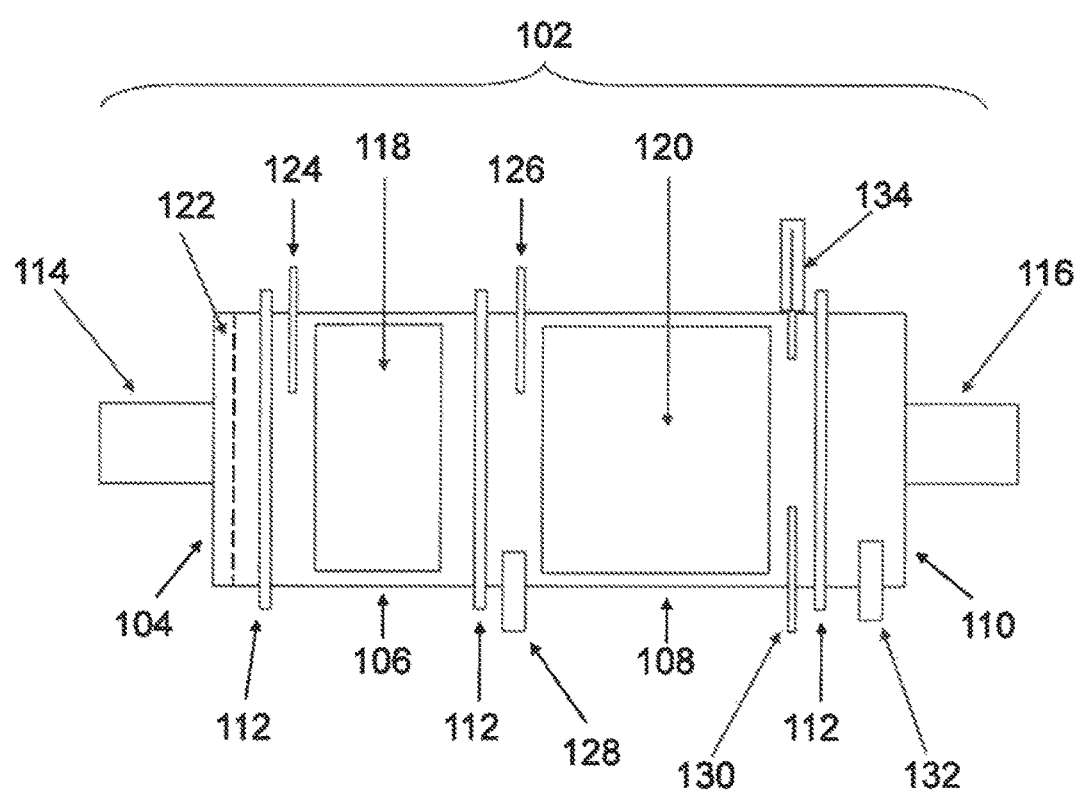
FIG. 1 is a simplified schematic side elevational view of a vehicle exhaust aftertreatment assembly containing at least one radio frequency sensor in accordance with the present invention.

FIG. 1 depicts an emissions aftertreatment assembly or system 102 which, in one example, is a diesel or gasoline particulate filter assembly that may or may not contain additional catalysts such as a three-way catalyst, oxidation catalyst, selective catalytic reduction system, or the like.

In another example, system 102 is a catalyst such as a three-way catalyst, oxidation catalyst, selective catalytic reduction catalyst, NOx trap, or the like and does not contain any type of filter.

In yet another example, system 102 contains one or more catalyst coatings applied to a filter, such as an oxidation catalyst on a filter, an SCR catalyst applied to a filter, or a TWC catalyst applied to a filter, or any other catalyst applied to a filter, forming a so-called multi-function filter.

Assembly 102 may be comprised of an inlet section 104, a first module or housing 106, a second module or housing 108, and an outlet section 110. An inlet conduit 114 is connected to inlet section 104 and an outlet conduit 116 is connected to outlet section 110. Inlet and outlet conduits 114 or 116 extend into inlet and outlet sections 104 or 110 respectively. Inlet and outlet sections 104 and 110 as well as modules 106 and 108 are connected via an interconnect 112 including for example a flange, a clamp, or the like.

Elements 118 and 120 are contained within modules or housings 106 and 108, respectively. Although two elements and modules am shown, multiple configurations are possible, with only one element and module, or more than one element and module, or multiple elements contained within a single module. In one embodiment, elements 118 and 120 are catalysts, filters, membranes, or some combination thereof.

In one example, element 118 is an oxidation catalyst, SCR catalyst, LNT or three-way catalyst, and element 120 is a gasoline or diesel particulate filter. Additional elements 122, such as baffles, passages, mixing plates or tubes, and the like, are contained within one or more sections, or modules. In one embodiment, the element 122 is a baffle or flow distribution plate. In another embodiment, element 122 is a radio frequency screen or mesh. When the element 122 is a radio frequency screen or mesh, it can be located either upstream in the assembly 102 and the module 106 as shown in FIG. 1, downstream in the assembly 102 and the module 108, or between the two modules 106 and 108.

The aftertreatment assembly 102 further comprises additional structures, probes, sensors, or other elements 124, 126, 128, 130, 132, or 134 extending into the interior of modules or housings 106 or 108 or inlet or outlet sections 104 or 110. In one embodiment, the additional structures 124, 126, 128 comprise temperature sensors and the additional structures 128 or 132 comprise oxygen sensors, NOx sensors, soot sensors, ammonia sensors, pressure sensors, or the like.

Probe 134 is a radio frequency measurement probe, such as a rod antenna loop antenna or waveguide, including dielectric waveguides, launchers and resonators that are robust and well-suited to harsh environment applications. Probe 134 is configured to transmit and receive radio frequency signals sufficient to generate one or more resonant modes within the assembly 102 or over any frequency range or ranges. One or more probes 134 may be used. Probe 134 can be located in several locations in the assembly 102 such as for example, upstream of the element 118, downstream of the element 120, between the elements 118 and 120, or even inside the elements 118 or 120. When multiple probes 134 are located in the assembly 102, they can be located in the same or different elements 118 and 120 and adapted to monitor the processes occurring in elements 118 and/or 120 and/or the processes occurring within the volume defined by the assembly 102 or a region of the assembly 102.

In another embodiment, probe 134 is a multi-function sensor including for example a combined radio frequency probe/sensor and temperature sensor. Probe 134 may also contain multiple integrated sensors such as for example temperature sensors, pressure sensors, chemical sensors, and/or particle sensors.

The radio frequency response of cavity assembly 102 is influenced by the geometry of the modules 106 and 108, the inlet and outlet sections 104 and 110 and the inner conducting elements, probes, sensors, and the like 122, 124, 126, 128, 130, 132, as well as the interconnects 112.

Interconnects 112 maintain structural stability to the assembly 102, seal the assembly 102 against leaks, and provide good electrical contact between the modules 106 and 108. Clamps or other shunting elements can be used to provide good electrical contact between the modules 106 and 108. The type of elements 118 and 120, as well as their position within modules 106 and 108, respectively, may also influence the radio frequency measurements. The geometry, location and mounting of the probe(s) 134 as well as the operation of a radio frequency control unit including attached cabling (not shown), may also affect the measurements.

The mesh 122 is in electrical contact with the assembly 102 and may be placed at different locations within the assembly 102 to shield or contain the radio frequency signal to a particular region of the assembly 102. In one embodiment, the mesh 122 may be placed between the elements 118 and 120, or between the element 120 and the outlet section 110 in order to isolate the radio frequency signal to probe filter or catalyst element 120 only. The mesh 122 may be a standard baffle, mixer or flow distribution plate, serving a number of purposes.

The mesh 122 or other suitable conducting element may be used to preferentially control or influence the electric field distribution within the assembly 102 such as for example to suppress or enhance selected resonant modes. The mesh 122 or other suitable conducting elements may be fixed, or variable. In one example, the mesh 122 or other conducting element may be used to enhance the resonant modes occurring on either element 118 or 120. In another example the mesh 122 or other conducting element may be used to suppress resonant modes or contain the field to only certain regions within cavity 120 to reduce the effect or external variables or noise sources on the measurements. The mesh or conducting element may serve more than one purpose. In one example the mesh or conducting element functions as a baffle, mixer, or flow distribution device, in addition to preferentially affecting the radio frequency signal.

The radio frequency probe 134 is used to monitor the radio frequency response of the assembly 102. The radio frequency response may consist of the radio frequency signal magnitude and/or phase. The frequency range utilized for the measurements may be any frequency range, and may or may not result in the establishment of resonance within cavity 102.

In one example, the frequency range may include multiple resonant modes, with each mode corresponding to a specific spatial or localized region of high electric field strength within the cavity 102. The radio frequency response to material accumulation in the cavity 102 is most sensitive to material accumulated in regions where the electric field is strongest. In one example, multiple resonant modes may be used to monitor the local loading state of the filter or catalyst. In another example, multiple resonant modes may be used to ensure the entire filter or catalyst volume is sampled to determine the total or aggregate change in filter loading. In this manner, the radio frequency sensing system monitors the entire exhaust stream and its interaction with the filter or catalyst.

Figure 2:
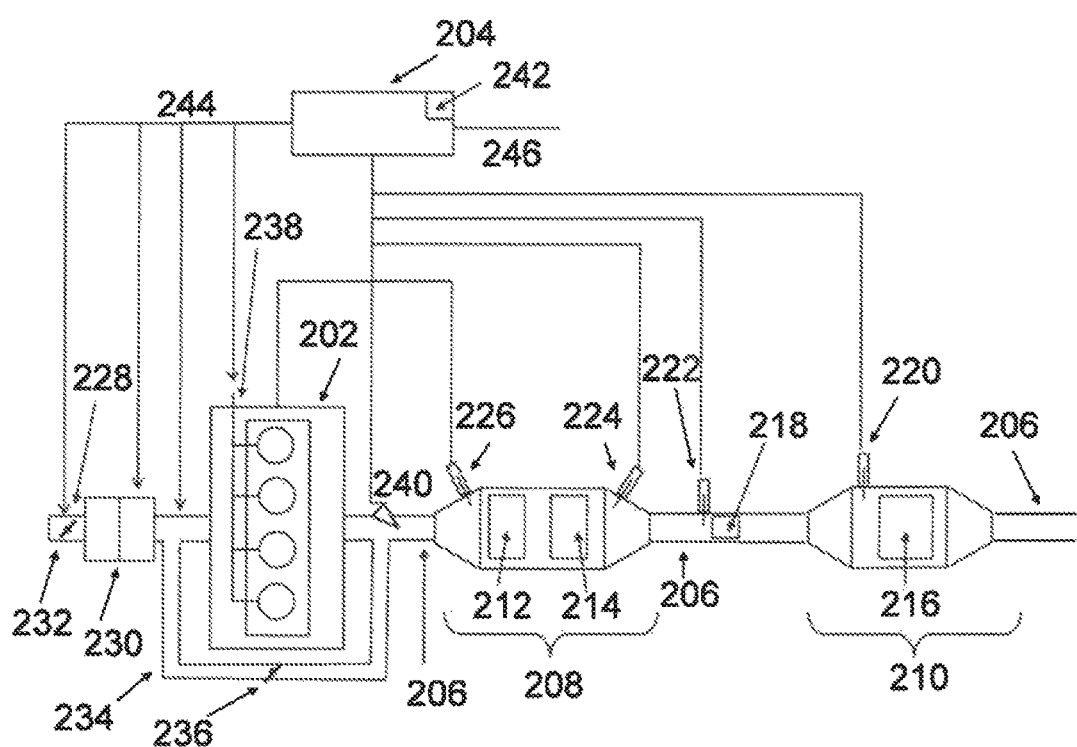
FIG. 2 is a simplified schematic side elevational view of a vehicle engine and exhaust system monitored by a radio frequency system in accordance with the present invention.

FIG. 2 shows a plant comprising for example an engine and exhaust system monitored by a radio frequency system. The plant may be any type of plant, such as a chemical plant, food processing plant, power plant, refinery, distillery, or any type of plant or process. The plant or reactor may be a flowing reactor, or it could be a batch reactor. A machine 202, such as an engine in one example or a plant in another example, has an outlet connection such as for example a conduit 206 connected to various components and sensors. Machine 202 generates an output stream, such as an exhaust stream, or any other stream, which is directed through conduit 206. In one embodiment, conduit 206 is connected to a first module 208 and a second module 210. In one embodiment, modules 208 and 210 may be cavities, such as resonant cavities, or may be waveguides in another embodiment.

In one particular embodiment, module 208 may be a particulate filter assembly such as the assembly 102 shown in FIG. 1 containing multiple elements such as for example a catalyst element 212 such as for example a three-way catalyst (TWC), oxidation catalyst (OC), selective catalytic reduction catalyst (SCR), lean NOx trap (LNT), or any type of catalyst, and a filter element 214 such as a particulate filter.

In one embodiment, module 210 is a catalyst housing containing a catalyst element 216 such as an SCR, LNT, TWC, ammonia storage, hydrocarbon trap, scrubber or any other type of catalyst.

In another embodiment, no modules 208 or 210 may be present and, in another embodiment, more than two modules 208 and 210 may be present. Each of the modules 208 and 210 may contain one or more elements, such as catalysts, filters or membranes in one example, or no internal elements in another example.

Conduit 206 contains one or more internal elements 218 such as a filter, catalyst, mixer, diffuser, or other element. The elements 218 may be located at any position within conduit 206. Radio frequency probes or sensors 220, 222, 224, and 226 such as rod antennas, loop antennas, waveguides, dielectric resonators, or any other suitable probes or sensors for transmitting and/or receiving radio frequency signals are mounted to and extend into conduit 206 and the modules 208 and 210.

Additional conduits 232 are connected to machine 202 including for example intake ducts, fuel lines, oil lines, coolant lines, or other similar conduits. Conduit 232 may supply an inlet stream to the plant or machine 202. Conduit 232 contains turbomachinery 230 including for example a turbocharger or supercharger. An exhaust gas recirculation (EGR) circuit 234 forms a fluid path between exhaust conduit 206 and inlet conduit 232. The EGR circuit 234 contains a valve 236 or other suitable flow control mechanism or actuator for regulating the exhaust flow. EGR circuit 234 may be either high or low pressure, internal or external, and may be cooled. The inlet conduit 232 contains a throttle or valve 228 for regulating intake flow.

Machine 202, if in the form of an engine, may contain one or more cylinders. Fuel may be supplied to the cylinders of machine 202 by means of a fuel delivery system 238 that can include a fuel supply tank, pumps, and injectors (not shown). The fuel supply system 238 is mechanically or electronically controlled by means of a control unit 204.

Although FIG. 2 depicts machine 202 as having one inlet conduit 232 and one outlet conduit 206, machine 202 may contain multiple or no inlet and outlet conduits. Each of the conduits 232 and 206 may consist of a network for connections, passages and conduits (not shown) such as a pipe or duct system or network consisting of interconnected conduits of varying sizes and geometries. Additional modules, such as multiple modules 208, 210, or 218, may or may not be present in inlet our outlet conduits.

Emission constituent dosing or injection devices, such as a doser 240 is present in the machine 202. In one embodiment, the doser 240 is a hydrocarbon doser for injection hydrocarbons used to initiate regeneration of the particulate filter 208. In another embodiment, the fuel injection system 238 is used to perform the same function. In another embodiment, doser 240 may be a urea doser or gaseous ammonia injector for supplying urea or ammonia to an SCR catalyst. Doser 240 may be positioned anywhere along the exhaust conduit. In one example where module 210 is an SCR catalyst, doser 240 may be a urea doser positioned in conduit 206 upstream of module 201 but downstream of module 208. In another example, doser 240 may be a hydrocarbon doser positioned upstream of the particulate filter.

Radio frequency probes 220, 222, 224, and 226 are connected to the engine control unit 204. A single or multiple control units 204 may be used to monitor and control all of the radio frequency probes. Additional sensors not shown, such as temperature sensors, pressure sensors, gas composition sensors (NOx, PM, Oxygen, Ammonia) or any other types of sensors may be used. These ancillary sensors may be connected to the control unit 204 or another control unit, such as an engine, plant, or process control unit, also not shown, which may be in communication with control unit 204.

Control unit 204 includes a processing unit and computer readable storage medium 242 that contains instructions, algorithms, data, lookup tables, and any other information necessary to control the connected sensors and machine. Control unit 204 also includes connections 244 and 246 comprising a communication connection, such as Ethernet, USB, analog, CAN, serial, or some other type of connection, wireless, or power connection. Connection 246 may be connected to the plant control unit, to the engine control unit (ECU) in a vehicle, or to signal to the operator of the status of the control unit and of potential problems.

Control unit 204 includes hardware or electronics for transmitting radio frequency signals, such as an oscillator or synthesizer, as well as a detector for detecting radio frequency signals such as a diode or power detector or any other type of detector. Control unit 204 may further contain mixers, splitters, directional couplers, switches, and other components for controlling, modulating, transmitting, and monitoring radio frequency signals. In another example, control unit 204 may be a network analyzer or spectrum analyzer.

Control unit 204 is configured to transmit and receive and control radio frequency signals through any of the radio frequency probes 220 222, 224, and 226. Each probe may be independently controlled to transmit, receive, or transmit and receive radio frequency signals, such as in a multi-port network including transmission, reflection, and transmission or reflection.

Control unit 204 is also configured to monitor changes in one or more of the emission constituents based on changes in one or more parameters of the radio frequency signals as discussed in more detail below.

Control unit 204 may further be configured to modify the operation of the engine, machine, or emissions after treatment system based on the radio frequency measurements and, more specifically based on changes in one or more of the parameters of the radio frequency signals. Examples of modifications to system operation include the triggering of fault conditions or changes to the engine operation, such as fueling, airflow, boost pressure, or any other process control parameter.

The radio frequency signals may span a frequency range to establish one or more resonant modes, or may span a frequency range that does not include a resonant mode, or may be at a single frequency or multiple discrete frequencies. The various modules 208, 210, and conduit 206 may serve as microwave resonant cavities or waveguides, or may contain resonators (such as dielectric resonators) that can be used to sample a limited region of the device being monitored.

The radio frequency signal, including resonance curve, absolute amplitude, relative amplitude (i.e., normalized to the power being transmitted by the probe), phase, resonant frequency shift, frequency shift, or some derivative thereof including local or absolute maxima or minima, frequency shift at resonance or away from resonance (such as a notch), phase shift, average value, quality factor, summation, area, peak width, or other parameter may be correlated to the state of the system and used by the control unit 204 to monitor changes in the loading state of the system.

Figure 3:
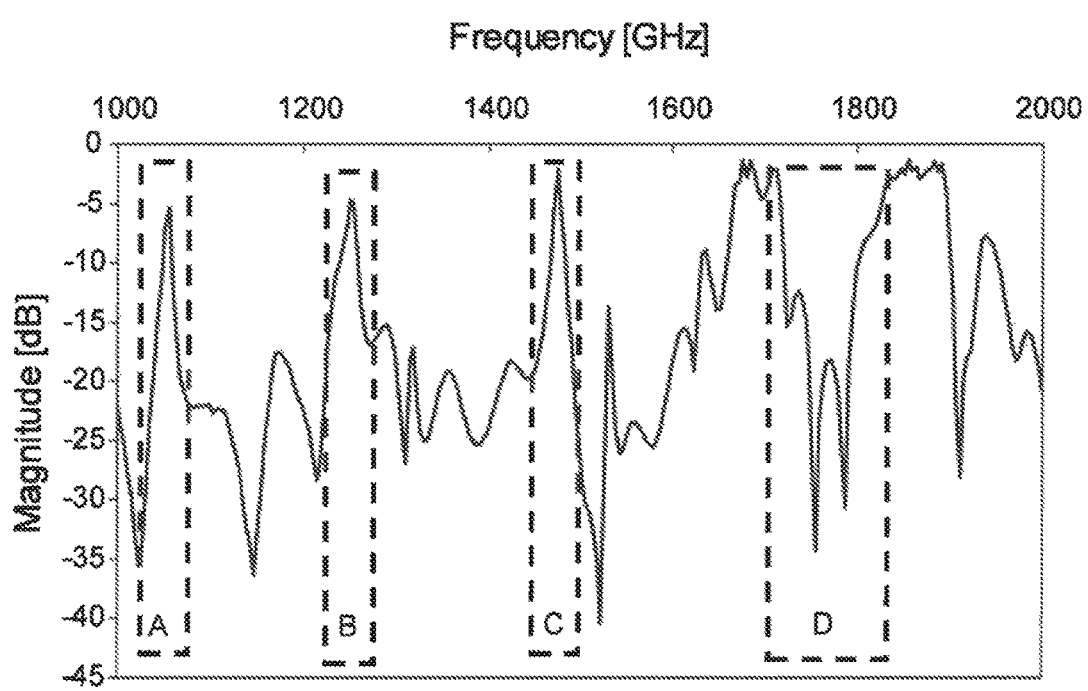
FIG. 3 is a graph representing one radio frequency sensor based method in accordance with the present invention for monitoring exhaust emissions.

In one method of operation of the system 102 and control unit 204 and as shown in FIG. 3, the radio frequency signal may span a broad frequency range sufficient to generate one or more resonant modes. In another embodiment, only certain regions of the broad frequency range may be sampled such as for example the regions generally designated as regions (A), (B), (C), and (D) in FIG. 3. The regions of interest may be pre-defined and selected based on one or more of the following criteria: reduced measurement time (faster response) by sampling only certain frequency ranges rather than monitoring the full resonance curve; monitoring only specific frequency bands, which may correspond to different spatial locations within the cavity; include only those frequency regions which are sensitive to the particular parameter being measured (contaminant material/emissions constituent type); or monitor only frequency bands which exhibit favorable behavior, such as monotonic behavior, for the parameter of interest.

Although the use of a broad frequency range is described, the range need not be broad. A narrow frequency range or even a single discrete frequency could also be used in some cases. Several frequency ranges or single frequencies could be used for a single measurement, with or without weighting or bias functions in order to improve the measurement characteristics.

In another embodiment, one or more narrow frequency ranges may be used to reduce the sensor response time. The use of narrow frequency ranges enables hopping between specific frequency bands, thereby increasing the speed of the measurements. The narrow frequency bands may correspond to specific resonant modes. Other means of increasing the measurement response time include reducing the overall frequency range or decreasing the number of points sampled across the frequency range.

In one embodiment, the measurements are conducted with high resolution at or near specific resonant modes or anti-resonances (valleys). Decreasing the time required to conduct the measurements is desirable to enable faster sensor response.

In another embodiment, only a portion of the resonance curve is sampled at a particular instance in time, such as regions (A) and (B) in FIG. 3, with a broader range of the resonance curve or the full curve sampled at a subsequent point in time.

In another embodiment, the power transmitted by one or more of the transmitting elements may be varied to improve the signal available for measurement. This variation in power output would be defined by operating conditions. The power output may be variable using a variable power output synthesizer or oscillator, or through the addition of an amplifier or attenuator or some other means of manipulating the power transmitted.

The radio frequency response may be characterized by the change in the magnitude and/or phase of the radio frequency signal, shift in frequency of the signal or any parameter derived or computed from the radio frequency signal phase, amplitude, or frequency.

Figure 4A:
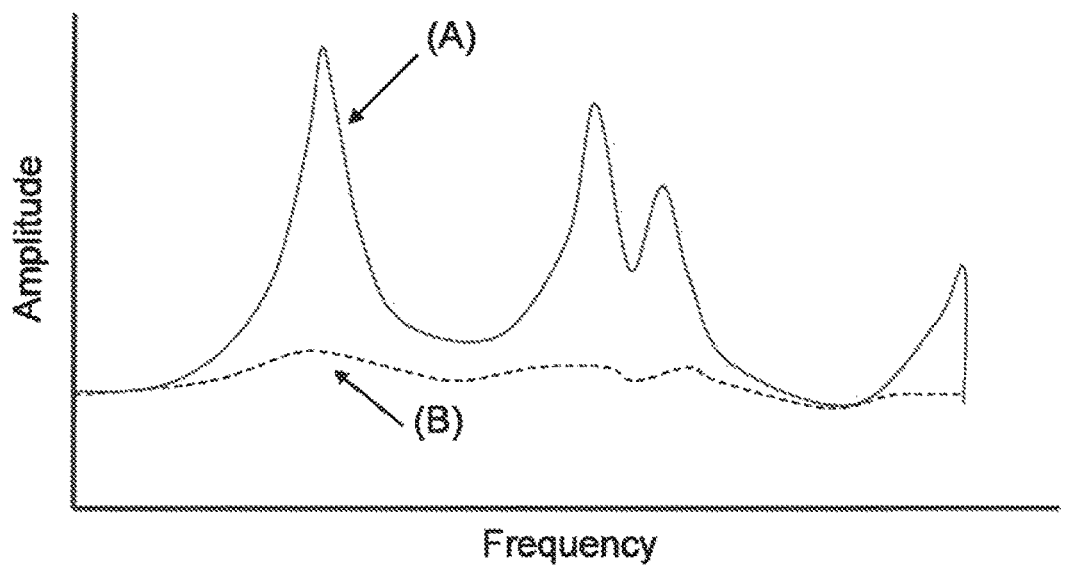
FIG. 4A is a graph representing the effect of an emissions constituent interacting with the filter or catalyst on the magnitude/amplitude of the radio frequency response over a given frequency range.

As shown in FIG. 4A, the effect of an emissions constituent accumulation in the particulate filter or storage or interaction of an emission constituent with the catalyst on the magnitude/amplitude response over a given frequency range relative to a clean filter or catalyst with no emissions constituent accumulation is represented by the two resonance states/curves (A) and (B) respectively. The changes to the resonance states (A) and (B) depend on the dielectric properties of the contaminant material as well as the material or media with which it interacts or displaces. The change in the resonance state shown in FIG. 4A may be to the amplitude or frequency.

In one example, as in the case of an emission constituent such as soot or ammonia, the accumulation of soot or ammonia on a particulate filter or catalyst respectively may result in a decrease in amplitude/magnitude of the resonance signal or a shift in the frequency of the resonance signal. In another example, as in the case of an emission constituent such as ash, the accumulation of ash on a particulate filter may not affect the amplitude but may result in only a frequency shift. In yet another example, the accumulation or storage of oxygen on a three way catalyst may produce the opposite behavior, resulting in an increase in amplitude when oxygen is present and a decrease in amplitude for the oxygen depleted state. Therefore, the specific resonance response will depend on the nature of the exhaust or emission constituent material and its interaction with the filter or catalyst.

Figure 4B:
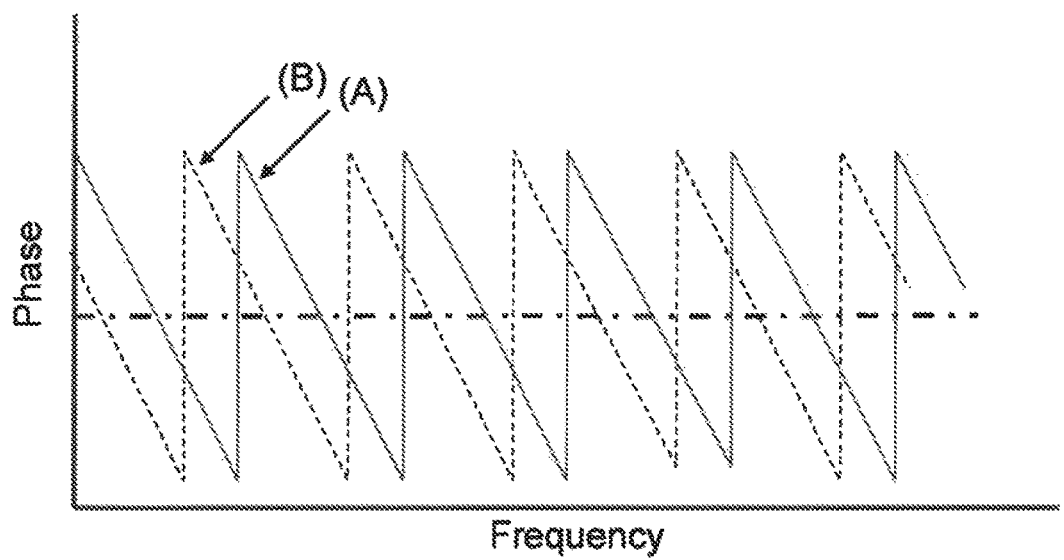
FIG. 4B is a graph representing the effect an emissions constituent interacting with the filter or catalyst on the phase of the radio frequency response over a given frequency range.

As shown in FIG. 4B, the accumulation of an exhaust constituent on the filter or catalyst may also result in a shift in the phase of the radio frequency signal as represented by the different curves (A) and (B) in FIG. 4B. The monitored phase may be absolute or relative. One advantage to use of the control unit 204 to monitor phase in addition to or in lieu of monitoring amplitude/magnitude is the fact that the amplitude signal may saturate at high particulate filter or catalyst loading levels, or due to system aging or poisoning, whereas the phase measurement provides a wider operating range as the phase shift may not suffer from the same saturation limitation.

In one example, the phase and/or magnitude/amplitude of the RF signal may be monitored at one frequency range which may be predefined to measure one contaminant material/emission constituent, while the phase and/or magnitude/amplitude of the RF signal may be monitored at another frequency range which may be predefined to measure another contaminant material or exhaust constituent species.

In a particular example, one type of contaminant material or exhaust/emission constituent may be monitored using the amplitude of the RF signal, whereas a second type of contaminant material or exhaust/emission constituent may be monitored by the phase of the RF signal.

In a further particular example, a contaminant material or exhaust/emission constituent may be monitored by a shift in frequency of the magnitude or phase of the RF signal.

In another particular example, different frequency regions of the magnitude of the RF signal may be used to monitor one or more emission constituents with a first frequency region of the magnitude of the RF signal used to monitor one emission constituent and a second frequency region of the magnitude of the RF signal used to monitor a second emission constituent.

In yet another particular example, different frequency regions of the phase of the RF signal may be used to monitor one or more emission constituents with a first frequency region of the phase of the RF signal used to monitor one emission constituent and a second frequency range of the phase of the RF signal used to monitor a second emission constituent.

In yet a further particular example, different RF signal characteristics may be used to monitor more than one emission constituent in the same frequency region, such as by monitoring a change in frequency (shift), change in magnitude, or change in phase of the RF signal.

In yet another example, the contaminant material/emission constituent monitored may be a solid, liquid, or gas-phase component. In another example, the frequency, amplitude, or phase measurement or parameter derived therefrom may related to the state of the catalyst, filter, or cavity such as its aging state, condition, health, or functionality.

Either measurement approach, utilizing magnitude/amplitude measurements, phase measurements, or both may be applied to determine emission constituent/particulate matter levels in the particulate filter, as well as monitor the rate of particulate matter accumulating on the filter or leaving the filter, either by escaping the filter or from oxidation. The monitored radio frequency parameter, such as the amplitude, frequency, or phase, or a parameter derived therefrom may be over any frequency range.

Similarly, either measurement approach, utilizing magnitude measurements, phase measurements, or both may be applied to determine the storage state of a catalyst, as well as monitor the rate of one or more exhaust constituents being removed from the catalyst through desorption, consumption, oxidation, or some other means. The magnitude and/or phase signals may be utilized directly or some derivative parameter thereof, such as the average, maximum, minimum, quality factor (Q), frequency shift, phase shift, Integral, or time derivative, may be computed and used to determine exhaust emission parameters such as for example engine-out emissions rates, filter or catalyst accumulation levels, rate of dosing or addition of an exhaust constituent to the exhaust stream (such as hydrocarbons or urea) or quantity of particulate matter lost from the filter or other gas or liquid species consumed by or lost from a catalyst.

The rate of change in the radio frequency signal may be calculated based on two or more radio frequency signal measurements or average over several radio frequency signal measurements. Other calculations based on current radio frequency signal measurements and historical radio frequency signal information may be employed.

Figure 5A:
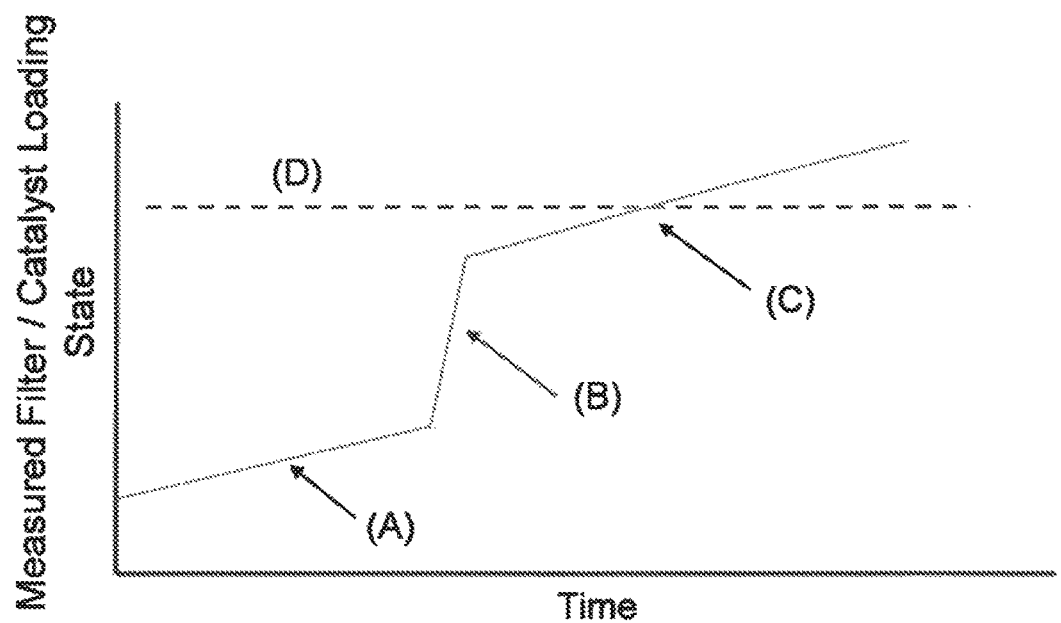
FIG. 5A is a graph representing the change in the measured emissions constituent accumulation or storage in the particulate filter or catalyst over time.
Figure 5B:
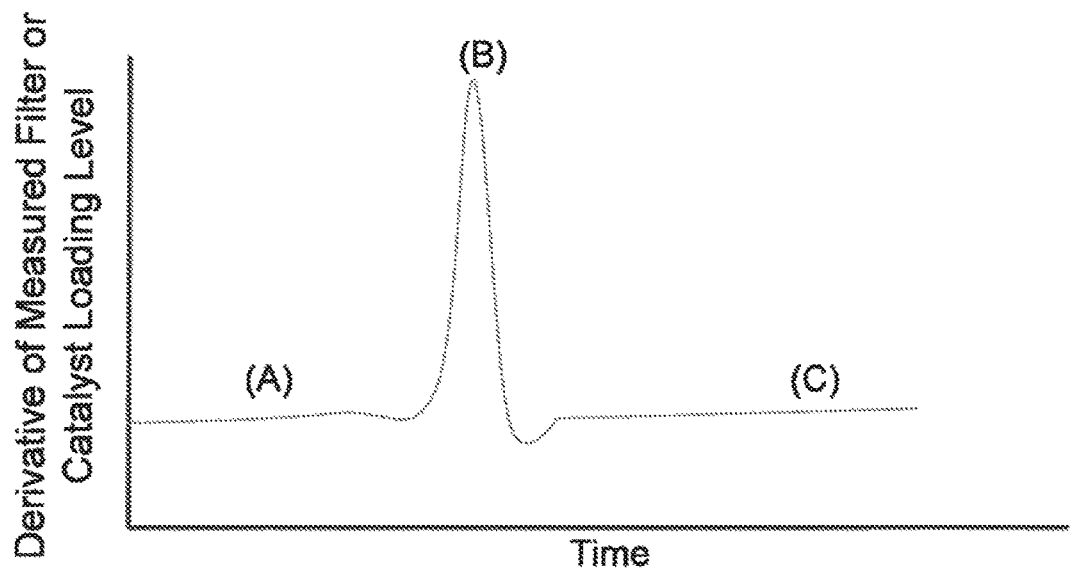
FIG. 5B is a graph representing the derivative of the change in the measured emissions constituent accumulation or storage in the particulate filter or catalyst over time.

FIGS. 5A and 5B provide examples of rate of change monitoring of the radio frequency signal with FIG. 5A depicting the rate of change in the total particulate filter or catalyst loading level and FIG. 5B depicting the corresponding rate of change derivative for three different operation regimes (A), (B), and (C). Regimes (A) and (C) show a lower level of exhaust constituent accumulation in the particulate filter or catalyst, whereas regime (B) shows a relatively high level of exhaust constituent accumulation.

In one exemplary embodiment, the change in filter particulate matter loading levels or catalyst storage levels may be computed and divided by the time (or some indication of relative time) between two or more radio frequency signal measurements. The resulting rate of change in the filter loading level or catalyst loading state may be related to the engine-out soot emissions in one example, the dosing rate of hydrocarbons or urea in another example, or the storage rate of oxygen, NOx, ammonia, or some other exhaust constituent on a catalyst in yet another example.

In this manner, the change in the radio frequency signal may be used to directly monitor engine-out soot levels by monitoring the change in the build-up of particulate matter on the filter, or monitor or control the rate of dosing of urea by monitoring the accumulation or storage of ammonia on the SCR catalyst in another example.

In yet another example, the engine out emissions rate of other solid, liquid, or gas phase emissions may similarly be monitored or controlled by the control unit 204 based on the determination of their time rate of change of the storage or loss of these species from the catalyst or filter. In one example, the change in the radio-frequency signal may be related to the engine-out soot emissions rate, with the particulate filter serving as an accumulation engine-out soot sensor probed or monitored by the radio frequency signal.

In another example, the change in the radio frequency signal may be related to the engine-out emissions rate of a gaseous species or exhaust constituent with the catalyst serving as engine-out gas sensors probed or monitored by radio frequency means. The approach therefore utilizes the filter or catalyst as the sensing element and enables the total or bulk engine-out emissions rate or exhaust constituent levels to be monitored.

In yet another example, the monitored rate of change of a particular exhaust constituent may be used to diagnose the operation of the system, by comparing the monitored rate of change with the expected rate of change. In one example, the operation of an oxidation catalyst may be diagnosed by comparing the monitored soot oxidation rate or oxidation rate of a particular exhaust species, with the expected oxidation rate. A slower than expected oxidation rate may be indicative of a loss in catalyst function or activity. Similarly, in another example, the catalyst storage capacity or uptake rate may be monitored, such as for oxygen storage on a three way catalyst, ammonia storage on an SCR catalyst, NOx storage on an LNT, or hydrocarbon storage on a hydrocarbon trap for example. Lower than expected storage rate may also be indicative of a loss in catalyst activity and used to diagnose or detect aged, poisoned, or faulty catalysts.

Monitoring multiple resonances further provides an indication of the local rate of change in the catalyst storage state or catalyst processes. In one example, a change in the location of the local (spatial) storage on the catalyst may indicate a loss in catalyst functionality locally. In one example, the location of the stored exhaust species on the catalyst may shift from being concentrated at the front of the catalyst toward the back of the catalyst as the catalyst ages or becomes poisoned. Monitoring this shift in local storage levels provides additional information on the health of the catalyst and may be used to diagnose the catalyst or filter operation. In another example, the shift in local storage levels may be radially, with differences between the center and periphery.

In another example, the rate of exhaust constituent storage may be used by the control unit 204 to diagnose the upstream processes such as the engine-out emissions. High levels or rates of storage on the catalyst or filter may indicate high engine-out emissions such as high soot emissions or high emissions of certain gas species such as NOx, hydrocarbons, carbon monoxide, or other gas species.

In one example, high engine-out NOx rates, determined either by a monitored high rate of NOx storage on a NOx trap or a high rate of ammonia consumption on an SCR catalyst, or a high rate of soot oxidation on a catalyzed particulate filter may be used to detect or diagnose engine conditions or faults resulting in high NOx emissions such as a faulty exhaust gas recirculation (EGR) system, incorrect combustion conditions, and the like. In a similar manner high engine-out soot emissions rates, detected by a high rate of soot accumulation on a particulate filter may be used to diagnose engine faults or malfunctions resulting in high soot emissions such as an injection system problem, poor combustion, lack of airflow, EGR malfunctions, and the like.

In another example, the diagnosed upstream processes need not be directly related to the engine, but may related to ancillary systems, such as hydrocarbon dosing systems or urea dosing systems. In one example, a comparison by the control unit 204 of the RF monitored rate of ammonia storage on the SCR catalyst with the expected rate of ammonia storage may be used to determine whether or not the urea or gaseous ammonia injection system is functioning property, or whether the correct quality or urea is being used. Similarly, the function of a hydrocarbon dosing system may be monitored by comparing the RF-monitored rate of soot oxidation on a particulate filter with the commanded hydrocarbon dosing level and expected soot oxidation rate. In another example, the same comparison may be used to determine the health of the catalyst.

The comparison of the monitored rate of change in the RF measured quantity on the catalyst or filter may be conducted with expected values from models or simulations, measurements from other sensors, stored values, such as in a lookup table, or any other suitable means. The comparison may be made at known operating conditions, over normal system operation (such as typical drive cycles or duty cycles characteristic of the application), or through intrusive testing by commanding a known change or impulse to the system and monitoring the system response.

Feedback from the monitored state or health of the filter or catalyst may also be used to initiate an action such as an alarm or trigger a fault code. In another example, the action may be used to compensate for a reduction in performance of the filter or catalyst system. In one example, the action may be to reduce the emissions of a specific exhaust constituent. In another example, the action may be to increase or decrease urea dosing or hydrocarbon dosing, or to increase the temperature of the system. Any number of actions may be employed to further diagnose or control, or improve the performance of the filter or catalyst based on the RF monitored performance.

The time response of the measurement defines the temporal resolution of the system. Response times of less than one second are readily achieved over a broad frequency range spanning up to 1 GHz and including over one thousand measurement points. Reducing the frequency range or number of measurement points can be used to decrease the measurement response time even further. Signal to noise ratio can be improved by using signal averaging or modifying the signal power output, such as by using an amplifier or variable gain, in another example. In yet another example, the signal to noise ratio may be improved by modifying the frequency range of operation.

In another example, the rate of change in the filter loading level may be related to the rate of soot oxidation on the particulate filter such as by filter regeneration, and in yet another example the rate of change in filter loading may be related to the rate of particulate matter escaping from the filter, such as from a failed filter.

In another example, different parameters may be computed from different resonant modes and, in yet another example, the rate of change of one or more resonant modes or resonant mode-derived parameters may be monitored which may or may not be from the same mode.

In another embodiment, knowledge of the engine operating parameters or operating history may be used to refine or improve the radio frequency signal measurements. In a particular embodiment, estimates of soot oxidation rates on the particulate filter, such as from soot oxidation models, or simple lookup tables based on the exhaust temperature, may be used to correct the radio frequency-based estimates of engine-out soot emissions levels. In one example, the amount of soot estimated to have oxidized over a specific period of time may be added to the radio frequency-based measurement of the change in particulate filter soot levels, thereby accounting for passive or active soot oxidation processes. In another example, the radio frequency measurements may only be carried out at low exhaust temperature conditions, such as below three hundred deg. C., or low NOx: PM ratios, where passive soot oxidation on the particulate filter may be negligible.

In yet another example, such as may be the case in a gasoline engine, the measurements may be carried out during conditions which are unsuitable for soot oxidation, such as oxygen-depleted conditions, in one example.

Similarly, the rate of consumption of other gaseous exhaust constituents may be monitored, such as the reduction of NOx emissions through the monitored consumption of ammonia on the SCR catalyst in one example or the oxidation of carbon monoxide or hydrocarbons through the monitored reduction in stored oxygen on a three way catalyst in another example. In a further example, the radio frequency measurements may only be carried out at conditions favorable for the measurements or conditions which allow for more accurate measurements of the monitored parameter. Many such conditions exist. In one example, the monitored rate of ammonia storage or consumption on the SCR catalyst may be carried out at low exhaust temperature where ammonia oxidation is negligible or when exhaust conditions are unfavorable for oxidation. Measurements may also be carried out at either lean or rich air fuel ratios which favor certain processes and inhibit others, or at low exhaust humidity, water, or moisture/condensate levels. In another example, corrections for one or more noise factors in the signal may be employed, such as applying a known offset or shift in the measured value based on knowledge of the system state or presence/absence of a particular noise factor.

Figure 6A:
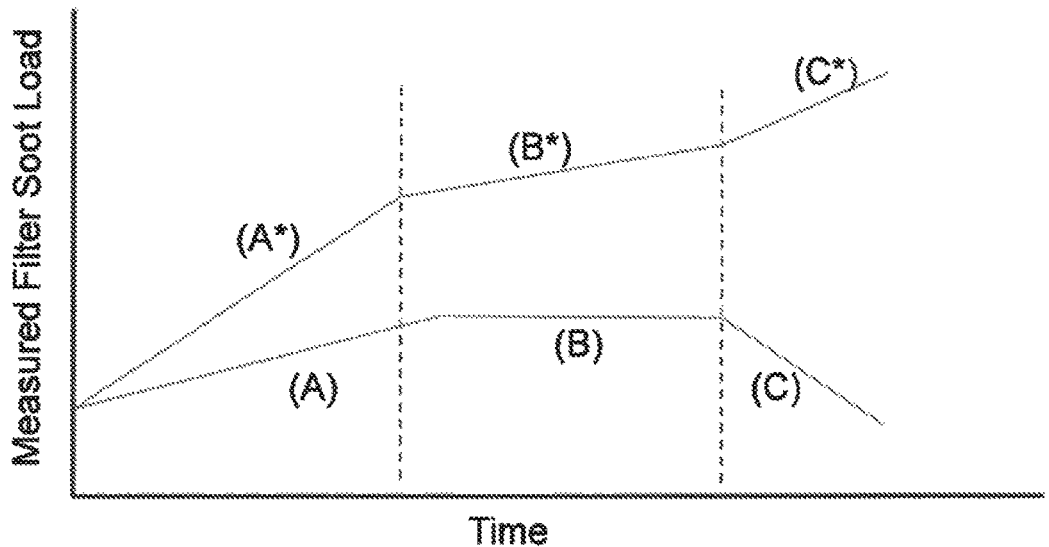
FIG. 6A is another graph representing the change in the measured emissions constituent accumulation or storage in the particulate filter or catalyst over time.
Figure 6B:
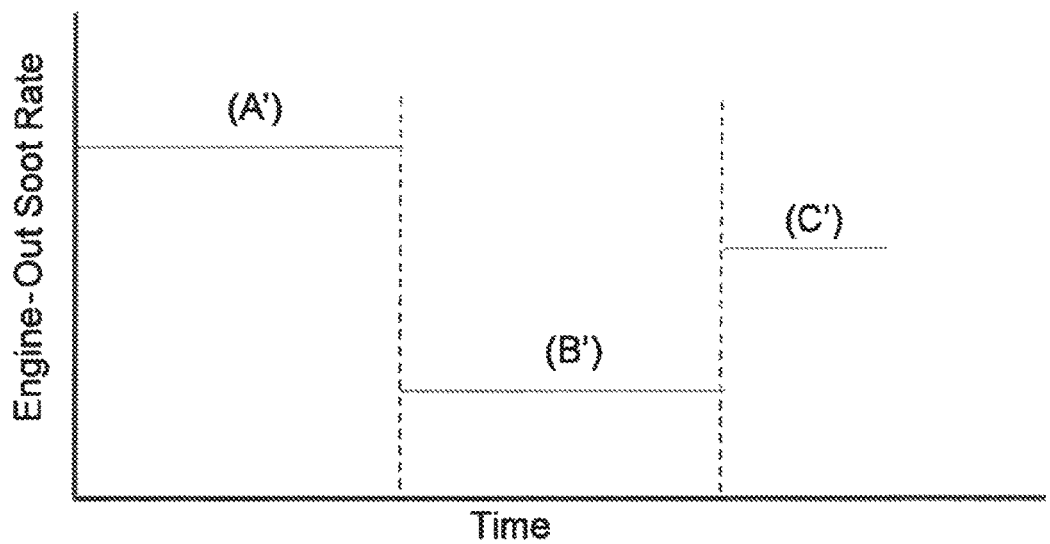
FIG. 6B is a graph representing the rate of change of an emissions constituent in the particulate filter or catalyst over time.

FIGS. 6A and 6B depict the monitored change in particulate filter soot levels or catalyst storage or loading levels using radio frequencies (i) with the rate of change in the emissions constituent (ii) in reference to three operational regimes (A), (B), and (C) in which regime (A) corresponds to a high level of a particular emissions constituent, (B) corresponds to an equilibrium condition where the accumulation or storage rate of the emissions constituent on the filter or catalyst is equal to the rate of consumption, oxidation, or loss of the emissions constituent, and (C) corresponds to a condition where the rate of the emissions constituent loss, consumption, or oxidation exceeds the rate of accumulation. FIG. 6A also depicts the radio frequency response after application of a correction for the soot oxidation on the filter or gas species oxidation or loss from the catalyst, indicated by the curves designated (A*), (B*), and (C*).

Implementing such an approach to account for soot oxidation or oxidation or consumption of a particular exhaust or emission constituent species, such as ammonia in one example, or oxygen in another example, therefore enables accurate measurements of engine-out soot emissions, or gas species emissions, or dosing based on the measured change in particulate filter soot loading levels, or catalyst storage levels, even for conditions where the overall soot levels in the filter or gas species on the catalyst are unchanging or decreasing.

Measurements from pressure sensors or temperature sensors in the exhaust system may further be used to correct the radio frequency signal in another embodiment, and measurements from gas sensors such as soot, NOx, or ammonia, or oxygen sensors, may be used to correct the radio frequency measurement in yet another embodiment. In another example, results of models or simulations, or stored values may be used to correct the signal.

In one example, measurements of exhaust temperature and NOx or oxygen concentrations may be used to infer a soot oxidation rate and correct the RF sensor measured soot accumulation on the filter or RF-measured engine-out soot levels in another example. In another example, the ammonia oxidation rate on an SCR catalyst or rate of consumption of oxygen on a three way catalyst may be inferred. In a further example, the correction may be made based on models or lookup tables and the like. In yet another example, the measurements from existing exhaust sensors or models (virtual sensors) may be used to determine conditions where soot oxidation is negligible or gas species oxidation stored on catalysts is negligible, and conditions are favorable for highly accurate RF measurements of soot accumulation rates on the filter or gas species storage rates on catalysts.

In another embodiment, measurements of engine-out exhaust constituents based on the radio frequency signal may further be used as a plausibility check for engine-out emissions models, or exhaust species oxidation models. In a particular embodiment, the radio frequency measurements may be used to improve the accuracy of engine-out emissions models used for comparison with measurements from downstream sensors such as soot sensors or ammonia sensors or NOx sensors for on-board diagnostic applications.

The engine-out emission constituent levels may be monitored over the course of normal engine operation. Abnormally high or low levels of engine-out constituent emissions may be used to diagnose engine or component failures or malfunctions such as faulty injectors, dosing system malfunctions, use of incorrect fluids, low or high EGR rates, intake or turbocharger problems, high oil consumption, control system problems, exhaust leaks, problems with the aftertreatment system, and the like.

In another example, engine operating parameters may be actively manipulated to generate a known level of engine-out constituent emissions, the accumulation on the particulate filter or catalyst thereof, may be detected and monitored by the changes in the radio frequency signal shown in FIGS. 4, 5, and 6. In one example, engine fueling, intake air, EGR, boost, injection timing, urea, ammonia, or hydrocarbon dosing or similar parameters may be modified to induce a change in the engine-out emissions constituents. Monitoring the rate of soot accumulation on the particulate filter or gaseous emissions storage on a catalyst either during or after such an intrusive test, provides information to diagnose the state of the filter or engine. The type, duration, and frequency of such an intrusive test may be fixed, or varied based on the circumstances. In one particular embodiment, such intrusive tests may be used for OBD purposes. In another embodiment, measurements of engine-out emissions determined from the radio frequency signal, may be used to modify or control the engine operation, such as the fueling or injection timing in one example, or the EGR rate or intake airflow in another example, or urea, ammonia, or hydrocarbon dosing in yet another example.

In another example, the rate of engine-out emissions measured by the change in the radio frequency signal may be used to monitor or diagnose the engine combustion process, or provide a feedback control loop to the engine combustion process or engine operation. The engine parameters that may be monitored or diagnosed include the intake air flow, fuel injection, injection timing, boost or turbomachinery operation, EGR systems, actuators, other sensors and control systems, and other parameters.

It is also possible to control the emissions constituents from the engine in order to improve the performance of the particulate filter or catalyst. For example, after a full regeneration it would be possible to adjust engine soot emissions in order to condition the filter, for example, establishing the cake layer on the surfaces of the filter. Monitoring of the filter is used to control emissions. In addition, it may be possible to set engine operation in order to adjust the soot characteristics, for example, by making soot with properties best suited to form the cake layer and prevent pore filtration, or generating soot with properties more or less favorable for oxidation in another example. In one example, the particle size may be controlled. In another example the particulate matter composition may be controlled include the soluble organic fraction. Once the filter has been conditioned, measured by the radio frequency sensing, the engine operation is returned to normal.

Similarly, it is also possible to control the constituent emissions from the engine to improve the performance of catalysts. In one example, the performance of the SCR catalyst may be improved through a de-sulfation event or regeneration to remove accumulated sulfur, which may be triggered based on the radio frequency signal measurements of catalyst performance. An increase in sulfur build-up may be detected directly through shifts in the radio frequency signal or through a reduction in ammonia storage or the rate of ammonia storage following a predetermined dosing event based on the local or global aggregate ammonia storage levels or rate of change in storage levels of ammonia. In another example, the SCR catalyst may be conditioned by managing the ammonia inventory to a specific level determined based on the RF measurements. Other examples include the modulation of air-to-fuel ration to achieve a specific amount of oxygen storage on a three-way catalyst. In yet another example, engine-out emissions may be modified to preferentially influence the catalyst processes such as soot oxidation (by increasing NOx or oxygen for example) or periodic rich or lean excursions, such as for passive ammonia generation in another example. In a particular example, the RF measurements may be used to control ammonia generation for a passive SCR system or so-called hydrocarbon SCR system.

In yet another embodiment, information regarding the engine operating parameters may be utilized to correct, refine, or optimize the radio frequency measurements. In a particular example the engine information includes engine speed, fueling, torque, EGR rate, intake air flow, and similar parameters.

The RF measurements of engine-out emissions may be determined based on the total aggregate change in filter loading levels or catalyst storage levels or the local change in filter loading or catalyst storage, based on the response of specific resonant modes or frequency ranges.

Numerous variations and modifications of the embodiment described above may be effected without departing from the spirit and scope of the novel features of the invention. It is to be understood that no limitations with respect to the radio frequency system and method for monitoring engine-out emissions described herein are intended or should be inferred. It is, of course, intended to cover by the appended claims all such modifications as fall within the scope of the claims.

What is claimed is:

1. A method for monitoring an emission constituent in a radio frequency system including a housing containing the emission constituent, one or more radio frequency sensors extending into the housing and transmitting and receiving radio frequency signals spanning a radio frequency range; and a control unit, the method comprising the step of controlling the radio frequency signals and monitoring changes in the emission constituent based on changes in one or more parameters of the radio frequency signals, and further comprising the step of sampling one or more of the parameters of the radio frequency signals in one or more predefined narrow radio frequency signal ranges to decrease the measurement response time.

2. The method of claim 1, further comprising the step of controlling the radio frequency signals and monitoring changes in one emission constituent based on changes in the magnitude or amplitude of the radio frequency signals and/or shifts in the phase of the radio frequency signals in one predefined radio frequency signal range and monitoring changes in another emission constituent based on changes in the magnitude or amplitude of the radio frequency signals and/or shifts in the phase of the radio frequency signals in another predefined radio frequency range.

3. The method of claim 1, further comprising the step of measuring changes in one or more of the parameters of the radio frequency signals in one or more predefined radio frequency signal ranges corresponding to one or more predefined spatial regions in the housing.

4. The method of claim 3, wherein the predefined spatial regions correspond to predefined spatial regions sensitive to the parameter of the radio frequency signal being measured.

5. The method of claim 3, wherein the predefined spatial regions correspond to predefined spatial regions exhibiting a favorable behavior for the parameter of the radio frequency signal being measured.

6. The method of claim 1, wherein the one or more predefined narrow radio frequency signal ranges correspond to one or more predefined resonant modes of the radio frequency signal.

7. The method of claim 1, further comprising the step of measuring a rate of change in one or more of the parameters of the radio frequency signals for monitoring a rate of change of the emission constituent.

8. The method of claim 1, further comprising the step of comparing the rate of change of the emission constituent with expected values of the rate of change of the emission constituent.

9. The method of claim 1, further comprising the step of monitoring the emission rate, accumulation rate, and/or depletion rate of the emission constituent.

\* \* \* \* \*